United States Patent
Bales

(10) Patent No.: US 6,746,488 B1
(45) Date of Patent: Jun. 8, 2004

(54) METHOD AND APPARATUS FOR HINDERING OSTEOLYSIS IN POROUS IMPLANTS

(75) Inventor: Joel Patrick Bales, Eads, TN (US)

(73) Assignee: Biomet, Inc., Warsaw, IN (US)

( * ) Notice: Subject to any disclaimer, the term of this patent is extended or adjusted under 35 U.S.C. 154(b) by 70 days.

(21) Appl. No.: 10/102,440

(22) Filed: Mar. 19, 2002

(51) Int. Cl.$^7$ .................................................. A61F 2/28
(52) U.S. Cl. ................... 623/23.51; 623/23.59; 623/23.75; 623/23.76; 623/16.11
(58) Field of Search ...................... 623/11.11, 16.11, 623/23.51, 23.57, 23.58, 23.59, 23.6, 23.74, 23.75, 23.76

(56) References Cited

U.S. PATENT DOCUMENTS

| | | |
|---|---|---|
| 4,644,942 A | 2/1987 | Sump |
| 4,957,819 A | 9/1990 | Kawahara et al. |
| 5,258,030 A | 11/1993 | Wolfarth et al. |
| 5,397,359 A | 3/1995 | Mittelmeier et al. |
| 5,405,389 A | 4/1995 | Conta et al. |
| 5,571,187 A | 11/1996 | Devanathan |
| 5,723,011 A | 3/1998 | Devanathan et al. |
| 5,926,685 A | 7/1999 | Krebs et al. |
| 5,993,716 A | 11/1999 | Draenert |
| 6,214,049 B1 * | 4/2001 | Gayer et al. ............. 623/16.11 |

* cited by examiner

*Primary Examiner*—Kevin Shaver
*Assistant Examiner*—Candice C. Melson
(74) *Attorney, Agent, or Firm*—Harness, Dickey & Pierce, P.L.C.

(57) ABSTRACT

A prosthetic implant, and method for making same, is described. The prosthetic implant preferably has a porous coating containing a plurality of pores therein. A biodegradable material is introduced into the pores, preferably under vacuum conditions, and substantially fills the pores. Because the pores are filled with the biodegradable material, they hinder infiltration of wear particles generated during loading of the prosthetic implant. Simultaneously, the biodegradable material permits infiltration of new bone tissue into the filled pores.

28 Claims, 2 Drawing Sheets

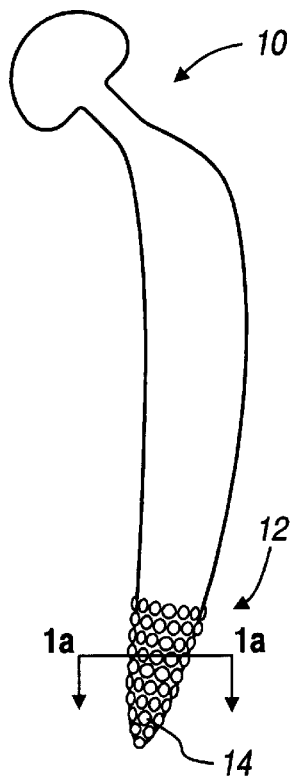
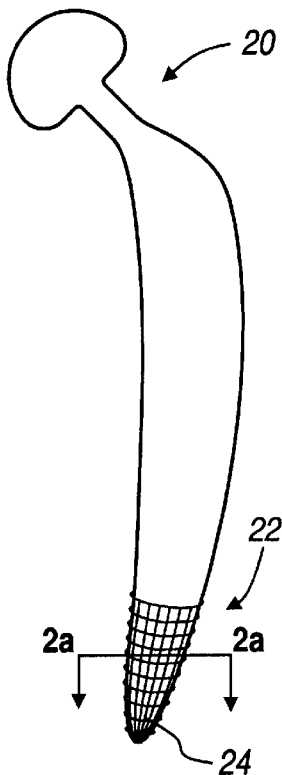
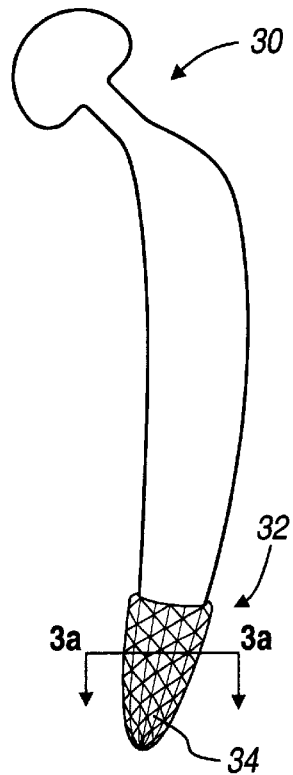
FIG.- 1
(PRIOR ART)
FIG.- 2
(PRIOR ART)
FIG.- 3
(PRIOR ART)
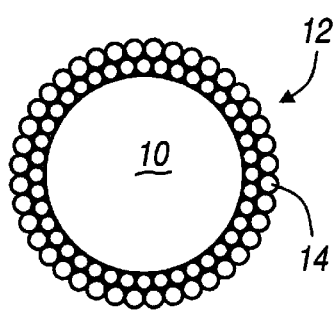
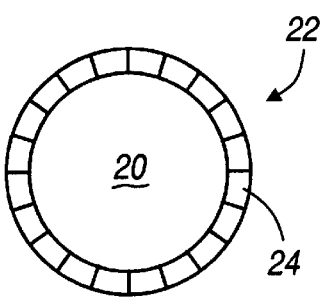
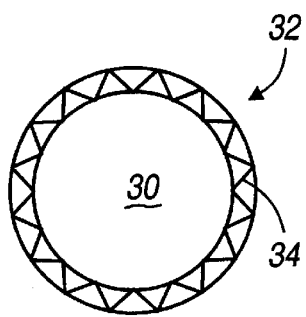
FIG.- 1a
(PRIOR ART)
FIG.- 2a
(PRIOR ART)
FIG.- 3a
(PRIOR ART)

METHOD AND APPARATUS FOR HINDERING OSTEOLYSIS IN POROUS IMPLANTS

BACKGROUND

The present invention relates generally to porous implants, and more particularly, to a new and improved porous implant and method for making same, wherein a biodegradable material is placed within the pores of the porous coating of the implant to hinder the migration of wear particles into these pores, thus aiding in the prevention of osteolysis at the implant site.

The use of various prosthetic implant systems, such as those used for the total replacement of knees and hips, has become increasingly more commonplace. For example, hip replacements are performed to alleviate conditions caused by osteoarthritis, rheumatoid arthritis, fractures, dislocations, congenital deformities, and other hip-related conditions.

Total hip arthroplasty involves replacing the damaged surfaces of the hip with artificial surfaces. Typically, the surgeon removes the head and neck of the femur and replaces them with a femoral component comprised of a metallic ball and stem. The damaged hip socket is lined with an acetabular component which is typically comprised of a metallic cup lined with a plastic material (such as polyethylene). The ball and stem fit into this cup, creating a new, movable hip joint.

Before 1983, most hip replacements in the United States were done using acrylic-based cements (e.g., polymethylmethacrylate) to attach the prosthetic components to the respective portions of the femur and pelvis of the patient. The area between the metal implant and the surrounding bone tissue was filled with acrylic cement. At that time, deterioration of the cement in some cases resulted in prosthetic loosening and recurrence of pain. In many cases, a revision operation, particularly with young and active patients was required. Unfortunately, when the revision operation was performed using acrylic cement, the success rate was lower than with the initial surgery.

In response to this problem, the prosthetic implant industry began to explore the feasibility of using porous-coated prosthetic implants, especially for use with active patients. The porous-coated method involves the use of implants with sintered metal porous surfaces. By way of a non-limiting example, beaded, sintered cobalt-chrome coatings may be used on a cobalt-chrome substrate, beaded, vacuum-sintered titanium coated may be used on a titanium substrate, or vacuum-sintered titanium fiber mesh pads may be used on a titanium substrate. Additionally, truss-like structures may be used on the substrate, as well. Typically, these porous coatings would be disposed on the surfaces of the prosthetic components in direct contact with the patient's bone tissue. For example, the stem portion of the femoral component and the outer surface of the acetabular component would be provided with these porous coatings.

Because cement is not required, these types of implants are sometimes referred to as either uncemented or cementless. As previously noted, the major difference between the porous-coated implants and the cemented implants is the metal surface of the porous-coated implants. Cemented implants typically have a smooth surface, and porous-coated implants have a rough surface resembling metal sandpaper. This porous surface allows surrounding bone tissue to grow into the pores of the porous coating, essentially making the implant a part of the patient's body. Close contact to the bone tissue helps hold the porous surfaced implant in place until bone ingrowth has occurred.

Unfortunately, all mechanical devices, including prosthetic implants, have a tendency to generate wear particles (e.g., debris) such as particles of plastic or metallic material from the prosthetic components. In porous implants, these wear particles can migrate down into the pores of the porous coating. This may occur during loading (e.g., walking, jumping, running, and so forth) wherein the axial motion may cause "pistoning" of the implant. The pores may soon contain these wear particles after the implant has been installed, thus hindering new bone tissue growth into the pores of the porous implant. As a result, a condition known as osteolysis may occur. Osteolysis is generally defined as a type of particulate induced bone resorption, wherein the immune response of the patient causes the surrounding bone tissue around the implant site to resorb away from the prosthetic component. Osteolysis can lead to aseptic loosening of the implant, and eventually, implant failure.

Therefore, there exists a porous implant, and method for making same, wherein the implant has a porous coating that is capable of preventing the infiltration of wear particles into the pores, but is simultaneously capable of permitting the ingrowth of new bone tissue into the pores.

SUMMARY OF THE INVENTION

In accordance with a first embodiment of the present invention, a prosthetic implant having a porous coating on at least a portion of a surface thereof is provided, wherein the porous coating has at least one pore formed therein, wherein loading of the prosthetic implant generates at least one wear particle, wherein the prosthetic implant is adjacent to a surface comprising bone tissue, comprising a biodegradable material disposed within the at least one pore. The biodegradable material hinders infiltration of the at least one wear particle into the at least one pore and permits infiltration of the bone tissue into the at least one pore.

In accordance with a second embodiment of the present invention, a prosthetic implant is provided, wherein loading of the prosthetic implant generates at least one wear particle, wherein the prosthetic implant is adjacent to a surface comprising bone tissue, comprising a porous coating disposed on at least a portion of a surface of the prosthetic implant, wherein the porous coating has at least one pore formed therein. A biodegradable material is disposed within the at least one pore. The biodegradable material hinders infiltration of the at least one wear particle into the at least one pore and permits infiltration of the bone tissue into the at least one pore.

In accordance with a third embodiment of the present invention, a prosthetic implant is provided, wherein loading of the prosthetic implant generates at least one wear particle, wherein the prosthetic implant is adjacent to a surface comprising bone tissue, comprising a substrate, a porous coating disposed on at least a portion of a surface of the substrate, wherein the porous coating has at least one pore formed therein, and a biodegradable material disposed within the at least one pore. The biodegradable material hinders infiltration of the at least one wear particle into the at least one pore and permits infiltration of the bone tissue into the at least one pore.

In accordance with a fourth embodiment of the present invention, a method of making a prosthetic implant having a porous coating on at least a portion of a surface thereof is provided, wherein the porous coating has at least one pore formed therein, wherein loading of the prosthetic implant generates at least one wear particle, wherein the prosthetic implant is adjacent to a surface comprising bone tissue, comprising disposing a biodegradable material within the at least one pore. The biodegradable material hinders infiltration of the at least one wear particle into the at least one pore and permits infiltration of the bone tissue into the at least one pore.

In accordance with a fifth embodiment of the present invention, a method of making a prosthetic implant is provided, wherein loading of the prosthetic implant generates at least one wear particle, wherein the prosthetic implant is adjacent to a surface comprising bone tissue, comprising disposing a porous coating on at least a portion of a surface of the prosthetic implant, wherein the porous coating has at least one pore formed therein, and disposing a biodegradable material within the at least one pore. The biodegradable material hinders infiltration of the at least one wear particle into the at least one pore and permits infiltration of the bone tissue into the at least one pore.

In accordance with a sixth embodiment of the present invention, a method of making a prosthetic implant is provided, wherein loading of the prosthetic implant generates at least one wear particle, wherein the prosthetic implant is adjacent to a surface comprising bone tissue, comprising providing a substrate, disposing a porous coating on at least a portion of a surface of the substrate, wherein the porous coating has at least one pore formed therein, and disposing a biodegradable material within the at least one pore. The biodegradable material hinders infiltration of the at least one wear particle into the at least one pore and permits infiltration of the bone tissue into the at least one pore.

A more complete appreciation of the present invention and its scope can be obtained from the following detailed description of the invention and the appended claims.

BRIEF DESCRIPTION OF THE DRAWINGS

The present invention will become more fully understood from the detailed description and the accompanying drawings, wherein:

FIG. 1 illustrates a perspective view of a prosthetic implant having a porous coating comprised of beads, in accordance with the prior art;

FIG. 1A illustrates a sectional view taken along line 1A—1A of FIG. 1, in accordance with the prior art;

FIG. 2 illustrates a perspective view of a prosthetic implant having a porous coating comprised of a mesh, in accordance with the prior art;

FIG. 2A illustrates a sectional view taken along line 2A—2A of FIG. 2, in accordance with the prior art;

FIG. 3 illustrates a perspective view of a prosthetic implant having a porous coating comprised of a truss, in accordance with the prior art;

FIG. 3A illustrates a sectional view taken along line 3A—3A of FIG. 3, in accordance with the prior art;

The same reference numerals refer to the same parts throughout the various Figures.

DETAILED DESCRIPTION OF THE INVENTION

Figure 4:
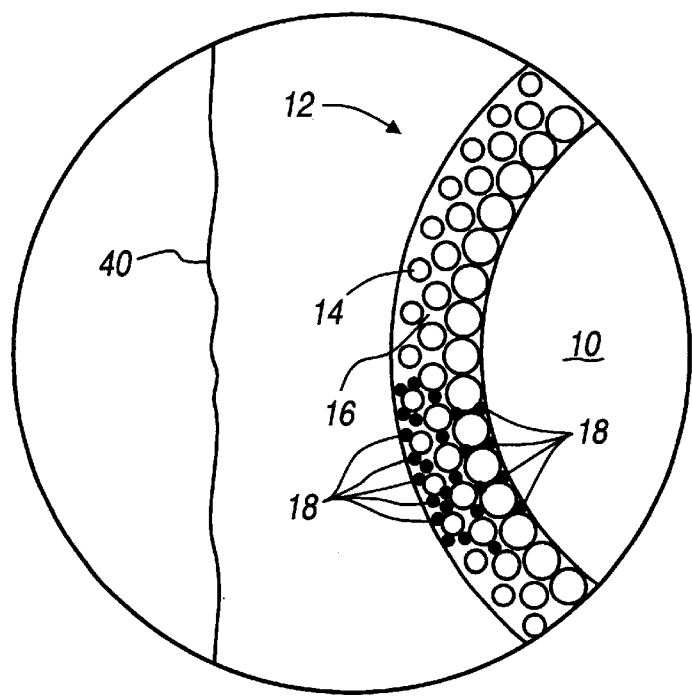
FIG. 4 illustrates an enlarged partial sectional of a portion of FIG. 1, in accordance with the prior art.

Although the present invention will be described primarily with respect to weight bearing prosthetic implants, such as those used for hip and knee replacement, it should be appreciated that the present invention is equally applicable for use with non-weight bearing prosthetic implants. Additionally, although the present invention is primarily intended to prevent the occurrence of osteolysis, it should be appreciated that the present invention is equally applicable for use in clinical situations where osteolysis is not likely to occur.

Referring to FIGS. 1, 1A, 2, 2A, 3, and 3A, there are shown perspective and partial sectional views of three illustrative prosthetic implants, 10, 20, and 30, respectively, in accordance with the prior art. In each case, the prosthetic implant 10, 20, and 30 is a femoral component used in hip replacement surgery.

Covering at least a portion of the external surface of each implant 10, 20, and 30 is a porous coating 12, 22, and 32, respectively. The porous coating 12, 22, and 32 can be in the form of beads 14, meshes 24, trusses 34, or any other suitable structure. The porous coating 12, 22, and 32, respectively, is typically applied to the prosthetic implant, 10, 20, and 30, respectively, and then sintered to ensure proper adhesion.

Referring to FIG. 4, there is shown an enlarged partial section of FIG. 1A, wherein a plurality of voids, recesses or pores 16 are visible throughout the various layers of the beads 14 of the porous coating 12. As previously noted, wear particles 18 (e.g., debris such as particles of plastic or metallic material from the prosthetic components) are typically generated during loading (e.g., walking, jumping, running, and so forth). These wear particles 18 can migrate down into the pores 16 of the porous coating 12. Because the pores 16 may contain these wear particles 18, thus hindering new bone tissue growth 40 to the pores 16 of the porous implant 10. This problem can potentially lead to osteolysis and eventual failure of the implant 10.

The present invention overcomes this problem by placing a biodegradable (i.e., resorbable, bioresorbable, or osteoinductive material) material within the pores of the implants. The implant may be immersed in the biodegradable material, or the biodegradable material may be sprayed on, rolled on, or otherwise applied to the porous coating. The biodegradable material is preferably introduced into the pores in a vacuum environment in order to ensure a proper amount of infiltration. Preferably, the biodegradable material completely, or at least substantially, fills the pore volume so as to prevent wear particles from infiltrating the pores in the first place. Additionally, because the material is biodegradable, it permits the ingrowth of new bone tissue into the pores, thus preventing, or at least delaying, the occurrence of osteolysis at the implant site.

Any suitable biodegradable material may be used to practice the present invention, provided that it prevents infiltration of wear particles into the pores, but simultaneously permits infiltration (i.e., ingrowth) of new bone tissue into the pores. However, it is preferred to employ tricalcium phosphate, polylactic acid, polyglycolic acid, and combinations thereof. One biodegradable material of particular interest is marketed by Biomet, Inc. (Warsaw, Ind.) under the trade name LACTOSORB®. LACTOSORB® is an absorbable co-polymer synthesized from all-natural ingredients: 82% L-lactic acid and 18% glycolic acid, unlike the homopolymers in common use such as 100% poly-L-lactic acid (PLLA) or 100% poly-glycolic acid (PGA), LACTOSORB® copolymer is substantially amorphous (i.e., without crystallinity), meaning that its degradation is uniform, precluding the crystalline release associated with degrading copolymers that have been associated with late inflammatory reactions.

Figure 5:
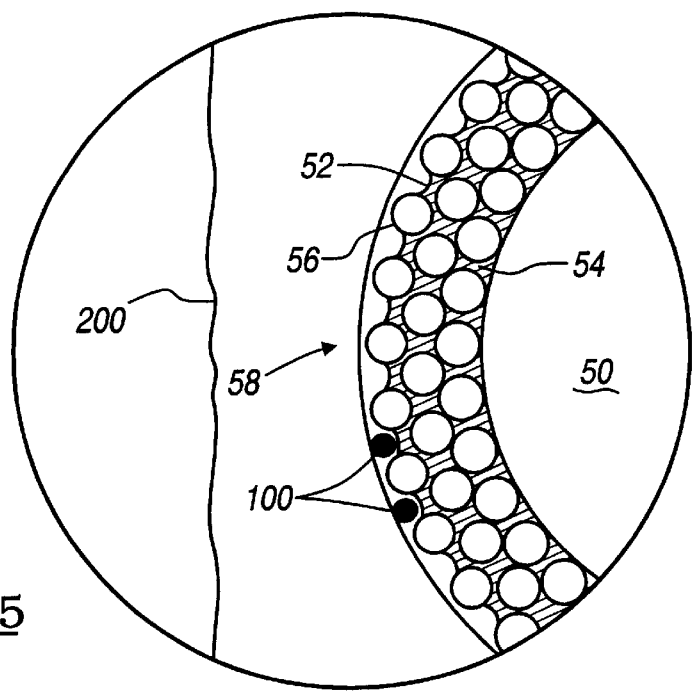
FIG. 5 illustrates an enlarged partial sectional of a prosthetic implant having a porous coating, wherein a biodegradable material has been disposed within the pores of the porous coating, in accordance with the general teachings of the present invention.

Referring to FIG. 5, there is shown enlarged partial sectional view of an implant 50 having a biodegradable material 52 disposed within the pores 54 of the beads 56 of the porous coating 58. Because the pores 54 are filled, any wear particles 100 can not infiltrate the pores 54, preserving the opportunity for new bone tissue 200 to grow into the pores 54 through the biodegradable material 52. The biodegradable material 52, thus, resists or hinders infiltration of the wear particles. Although the biodegradable material 52 is shown in use with beads 56, it should be appreciated that the biodegradable material 52 may be used to fill any type of pore formed by any number of different types of porous material (e.g., meshes, trusses, and so forth).

The foregoing description is considered illustrative only of the principles of the invention. Furthermore, because numerous modifications and changes will readily occur to those skilled in the art, it is not desired to limit the invention to the exact construction and process shown as described above. Accordingly, all suitable modifications and equivalents that may be resorted to that fall within the scope of the invention as defined by the claims that follow.

What is claimed is:

1. A prosthetic implant having a porous coating on at least a portion of a surface thereof, wherein the porous coating has a plurality of exposed pores formed therein, wherein loading of the prosthetic implant generates at least one wear particle, wherein the prosthetic implant is adjacent to a surface containing bone tissue, comprising:
   a biodegradable material disposed within a substantial number of exposed pores, thereby making the porous coating substantially non-porous;
   wherein the biodegradable material hinders infiltration of the at least one wear particle into the exposed pores;
   wherein the biodegradable material resorbs and permits infiltration of the bone tissue into the exposed pores.

2. The invention according to claim 1, wherein the biodegradable material substantially fills the at least one pore.

3. The invention according to claim 1, wherein the biodegradable material is comprised of materials selected from the group consisting of polylactic acid, polyglycolic acid, tricalcium phosphate, and combinations thereof.

4. The invention according to claim 1, wherein the biodegradable material is disposed in the at least one pore in a vacuum environment.

5. The invention according to claim 1, wherein porous coating is comprised of a metallic material.

6. The invention according to claim 5, wherein the metallic material has a structure selected from the group consisting of beads, meshes, trusses, and combinations thereof.

7. The invention according to claim 1, wherein the prosthetic implant is installed in a weight-bearing location on the human body.

8. The invention according to claim 7, wherein the weight-bearing location is selected from the group consisting of a hip, a knee, an elbow, a finger, a shoulder, an ankle, a wrist, and combinations thereof.

9. A prosthetic implant, wherein loading of the prosthetic implant generates at least one wear particle, wherein the prosthetic implant is adjacent to a surface having bone tissue, comprising:
   a porous coating disposed on at least a portion of a surface of the prosthetic implant, wherein the porous coating has a plurality of exposed pores thereon;
   a biodegradable material disposed within the plurality of exposed pores so as to substantially fill the pores;
   wherein the biodegradable material hinders infiltration of the at least one wear particle into the exposed pores;
   wherein the biodegradable material permits infiltration of the bone tissue into the exposed pores.

10. The invention according to claim 9, wherein the biodegradable material substantially fills the at least one pore.

11. The invention according to claim 9, wherein the biodegradable material is comprised of materials selected from the group consisting of polylactic acid, polyglycolic acid, tricalcium phosphate, and combinations thereof.

12. The invention according to claim 9, wherein the biodegradable material is disposed in the at least one pore in a vacuum environment.

13. The invention according to claim 9, wherein porous coating is comprised of a metallic material.

14. The invention according to claim 13, wherein the metallic material has a structure selected from the group consisting of beads, meshes, trusses, and combinations thereof.

15. The invention according to claim 9, wherein the prosthetic implant is installed in a weight-bearing location on the human body.

16. The invention according to claim 15, wherein the weight-bearing location is selected from the group consisting of a hip, a knee, an elbow, a finger, a shoulder, an ankle, a wrist, and combinations thereof.

17. A prosthetic implant, wherein loading of the prosthetic implant generates at least one wear particle, wherein the prosthetic implant is adjacent to a surface having bone tissue, comprising:
   a substrate;
   a porous coating disposed on at least a portion of a surface of the substrate, wherein the porous coating defines a porous surface;
   a biodegradable material disposed within the porous surface so as to make the porous surface substantially non-porous;
   wherein the biodegradable material hinders infiltration of the at least one wear particle into the porous surface;
   wherein the biodegradable material permits infiltration of the bone tissue into the porous surfaces.

18. The invention according to claim 17, wherein substrate is comprised of a metallic material.

19. The invention according to claim 17, wherein porous coating is comprised of a metallic material.

20. The invention according to claim 19, wherein the metallic material has a structure selected from the group consisting of beads, meshes, trusses, and combinations thereof.

21. The invention according to claim 17, wherein the biodegradable material substantially fills the at least one pore.

22. The invention according to claim 17, wherein the biodegradable material is comprised of materials selected from the group consisting of polylactic acid, polyglycolic acid, tricalcium phosphate, and combinations thereof.

23. The invention according to claim 17, wherein the biodegradable material is disposed in the at least one pore in a vacuum environment.

24. The invention according to claim 17, wherein the prosthetic implant is installed in a weight-bearing location on the human body.

25. The invention according to claim 24, wherein the weight-bearing location is selected from the group consisting of a hip, a knee, an elbow, a finger, a shoulder, an ankle, a wrist, and combinations thereof.

26. A method of making a prosthetic implant having a porous coating on at least a portion of a surface thereof, wherein the porous coating has a plurality of exposed pores formed therein, wherein loading of the prosthetic implant generates wear particles, wherein the prosthetic implant is adjacent to a surface having bone tissue, comprising:

disposing a biodegradable material within the exposed pores so as to make them substantially non-porous;

wherein the biodegradable material substantially hinders infiltration of the wear particles into the at least one pore;

wherein the biodegradable material permits infiltration of the bone tissue into the exposed pores.

27. A method of making a prosthetic implant, wherein loading of the prosthetic implant generates at least one wear particle, wherein the prosthetic implant is adjacent to a surface having bone tissue, comprising:

disposing a porous coating on at least a portion of a surface of the prosthetic implant, wherein the porous coating has at least one exposed pore formed therein;

disposing a biodegradable material within the at least one exposed pore;

wherein the biodegradable material hinders infiltration of the at least one wear particle into the at least one exposed pore;

wherein the biodegradable material permits infiltration of the bone tissue into the at least one exposed pore.

28. A method of making a prosthetic implant, wherein loading of the prosthetic implant generates at least one wear particle, wherein the prosthetic implant is adjacent to a surface having bone tissue, comprising:

providing a substrate;

disposing a porous coating on at least a portion of a surface of the substrate, wherein the porous coating defines an exposed porous surface thereon;

disposing a biodegradable material within the exposed porous surface so as to make it substantially non-porous;

wherein the biodegradable material hinders infiltration of the at least one wear particle into the porous surface;

wherein the biodegradable material permits infiltration of the bone tissue into the porous surface, after resorption of the biodegradable material.

* * * * *

UNITED STATES PATENT AND TRADEMARK OFFICE
CERTIFICATE OF CORRECTION

PATENT NO. : 6,746,488 B1  
DATED : June 8, 2004  
INVENTOR(S) : Joel Patrick Bales It is certified that error appears in the above-identified patent and that said Letters Patent is hereby corrected as shown below:

Column 1,  
Line 50, "coated" should be -- coating --.

Column 3,  
Lines 54 and 56, after "sectional" insert -- view --.

Column 5,  
Lines 29 and 61, after "is" insert -- adapted to be --.

Column 6,  
Line 30, after "is" insert -- adapted to be --.

Column 7,  
Lines 5-6 and 17, after "is" insert -- adapted to be --.

Column 8,  
Line 8, after "is" insert -- adapted to be --.

Signed and Sealed this

Third Day of May, 2005

JON W. DUDAS  
*Director of the United States Patent and Trademark Office*